United States Patent
Chinta et al.

(10) Patent No.: US 9,371,257 B2
(45) Date of Patent: *Jun. 21, 2016

(54) REACTORS AND PROCESSES FOR THE OXIDATIVE COUPLING OF HYDROCARBONS

(71) Applicant: FINA TECHNOLOGY, INC., Houston, TX (US)

(72) Inventors: Sivadinarayana Chinta, Sugar Land, TX (US); Joseph L. Thorman, Helsinki (FI)

(73) Assignee: Fina Technology, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/619,477

(22) Filed: Feb. 11, 2015

(65) Prior Publication Data

US 2015/0152026 A1 Jun. 4, 2015

Related U.S. Application Data

(60) Continuation of application No. 13/754,017, filed on Jan. 30, 2013, now Pat. No. 8,999,258, which is a division of application No. 12/763,233, filed on Apr. 20, 2010, now Pat. No. 8,399,726.

(51) Int. Cl.
*C07C 2/00* (2006.01)
*C07C 2/54* (2006.01)
(Continued)

(52) U.S. Cl.
CPC ... *C07C 2/84* (2013.01); *B01J 8/02* (2013.01); *B01J 8/18* (2013.01); *B01J 19/02* (2013.01); *B01J 23/002* (2013.01); *B01J 23/02* (2013.01); *B01J 23/34* (2013.01); *B01J 37/0201* (2013.01); *B01J 37/031* (2013.01); *C07C 2/64* (2013.01); *C07C 5/327* (2013.01); *B01J 2219/00006* (2013.01); *B01J 2219/025* (2013.01); *B01J 2219/0209* (2013.01); *B01J 2219/0218* (2013.01); *B01J 2523/00* (2013.01);
(Continued)

(58) Field of Classification Search
CPC ...... B01J 19/00; B01J 19/002; B01J 19/0026; B01J 19/02; B01J 2219/00; B01J 2219/00049; B01J 2219/00051; B01J 2219/0015; B01J 2219/00155; B01J 2219/02; B01J 2219/0204; B01J 2219/0218; B01J 2219/0236; B01J 2219/024; B01J 2219/025; B01J 2219/0277; B01J 2219/0281; C07C 2/00; C07C 2/54; C07C 2/64; C07C 2/74; C07C 2/82; C07C 8/84; C07C 5/00; C07C 5/32; C07C 5/327; C07C 5/333

See application file for complete search history.

(56) References Cited

U.S. PATENT DOCUMENTS

| | | | | |
|---|---|---|---|---|
| 4,447,656 A | * | 5/1984 | Kershner | C07C 37/07 568/722 |
| 5,430,219 A | * | 7/1995 | Sanfilippo | C07C 2/84 585/310 |
| 8,999,258 B2 | * | 4/2015 | Chinta | B01J 8/02 422/129 |

*Primary Examiner* — Natasha Young
(74) *Attorney, Agent, or Firm* — Albert Shung

(57) ABSTRACT

A method for the oxidative coupling of hydrocarbons includes providing an oxidative catalyst inside a reactor and carrying out the oxidative coupling reaction under a set of reaction conditions. The reactor surfaces that contact the reactants and products do not provide a significant detrimental catalyzing effect. In an embodiment the reactor contains an inert lining or a portion of the reactor inner surface is treated to reduce the detrimental catalytic effects. In an embodiment the reactor contains a lining that includes an oxidative catalyst.

20 Claims, 2 Drawing Sheets

(51) Int. Cl.
*C07C 2/64* (2006.01)
*C07C 2/74* (2006.01)
*C07C 2/76* (2006.01)
*C07C 2/82* (2006.01)
*C07C 2/84* (2006.01)
*C07C 5/00* (2006.01)
*C07C 5/32* (2006.01)
*C07C 5/327* (2006.01)
*C07C 5/333* (2006.01)
*B01J 19/02* (2006.01)
*B01J 8/02* (2006.01)
*B01J 8/18* (2006.01)
*B01J 23/00* (2006.01)
*B01J 23/02* (2006.01)
*B01J 23/34* (2006.01)
*B01J 37/02* (2006.01)
*B01J 37/03* (2006.01)
*B01J 19/00* (2006.01)

(52) U.S. Cl.
CPC .......... *C07C2521/10* (2013.01); *C07C 2523/02* (2013.01); *C07C 2523/30* (2013.01); *C07C 2523/34* (2013.01); *Y02P 20/52* (2015.11)

REACTORS AND PROCESSES FOR THE OXIDATIVE COUPLING OF HYDROCARBONS

CROSS-REFERENCE TO RELATED APPLICATIONS

This application is a continuation of U.S. patent application Ser. No. 13/754,017, filed on Jan. 30, 2013, now issued as U.S. Pat. No. 8,999,258, which is a divisional of U.S. application Ser. No. 12/763,233, filed on Apr. 20, 2010, now issued as U.S. Pat. No. 8,399,726.

The present invention is related to co-pending applications titled: Catalysts For Oxidative Coupling Of Hydrocarbons (Ser. No. 12/494,088); Process For The Oxidative Coupling Of Methane (Ser. No. 12/494,117); and Process For The Oxidative Coupling Of Hydrocarbons (Ser. No. 12/494,138) each filed by Fina Technology, Inc. on Jun. 29, 2009.

FIELD

The present invention generally relates to the oxidative coupling of hydrocarbons.

BACKGROUND

Polystyrene is a plastic used in many applications. The plastic can be extruded, injection molded, or blow molded to make objects like plastic cups and utensils, and casings for CDs. Polystyrene can also be formed with a rubber such as polybutadiene to make high impact polystyrene, or HIPS, which is more resistant to impact than normal polystyrene. HIPS can be used in toys, casings for appliances, and containers for food and medical supplies. One of the most recognizable forms of polystyrene is its foamed form, which can be used in packing materials and can be molded into containers, plates, cups and other shapes.

The monomer styrene is commonly produced via the dehydrogenation of ethylbenzene. This reaction can have several drawbacks, one being the formation of side products, such as benzene, toluene, and unreacted ethylbenzene. Another drawback is that ethylbenzene and styrene have similar boiling points, which can make their separation difficult.

Ethylbenzene, in turn, is generally produced via the alkylation of benzene with ethylene. The reaction can create several side products, such as polyalkylated benzene. One significant drawback to this reaction is the relatively expensive reactants that are required. Both ethylene and benzene can be obtained from refined petroleum. Ethylene is obtained predominantly from the thermal cracking of hydrocarbons, such as ethane, propane, butane, or naphtha, and generally goes through several cycles of distillation to obtain a certain purity level. Ethylene from these sources can include a variety of undesired products, including diolefins and acetylene, which can be costly to separate from the ethylene. Thermal cracking and separation technologies for the production of relatively pure ethylene can result in significant production costs.

Other methods for producing styrene include the oxidative coupling of hydrocarbons. This oxidative coupling reaction takes place in the presence of oxygen at elevated temperatures. Using an oxidative coupling reaction, styrene can be produced from toluene and methane. Historically, however, this process has suffered from low selectivity. Such low selectivity can lead to increased costs in order to achieve the desired product amount.

The costs associated with the production of polystyrene can be considered significant. Production relying on the alkylation of benzene with ethylene and the dehydrogenation of ethylbenzene for obtaining the monomer styrene can be cost intensive. Other methods, such as oxidative reactions, may use less expensive starting materials, however, these methods can suffer from low product selectivity. It would be desirable to have alternate methods for the production of ethylbenzene and styrene that increase product selectivity and that are consequently more economical.

SUMMARY

Embodiments of the present invention can include a reactor for use in carrying out the oxidative coupling of hydrocarbons. The embodiments of the present invention also can include a method for the oxidative coupling of hydrocarbons, such as the oxidative coupling of methane. The method can include the steps of preparing oxidative catalysts and running the oxidative coupling reaction inside the reactor over the oxidative catalyst, according to a set of reaction conditions.

An embodiment of the present invention includes a reactor that supports the oxidative coupling of hydrocarbons by reducing the reactor components from catalyzing the hydrocarbons under oxidative reaction conditions. The reactor of the present invention may have an inner coating or lining, which is capable of isolating the oxidative coupling reaction from contact with at least a portion of the interior walls of the reactor. In an embodiment, the coating or lining covers the majority of the parts that come into contact with the reaction mixture (also referred to as "wetted" parts) of the interior of the reactor. In an embodiment, the coating or lining may include a ceramic material, an inert sealant material, glass, quartz or combinations thereof. In an embodiment the reactor contains a coating or lining that includes an oxidative catalyst. In an embodiment at least a portion of the wetted parts of the interior of the reactor is treated to reduce the catalytic effects of the reactor interior, such as with the use of a passivation agent. In an embodiment at least a portion of the wetted parts of the interior of the reactor is treated to reduce any detrimental catalytic effects of the reactor interior.

In an embodiment of the present invention the reactor contains an oxidative catalyst. In a further embodiment the oxidative catalyst is prepared to influence the conversion, selectivity, and yield of the oxidative coupling of methane and other hydrocarbons. In another aspect, the oxidative catalyst is prepared to influence the conversion, selectivity, and yield of the oxidative coupling of methane to toluene.

The reactor of the invention can include a reaction zone under reaction conditions containing a catalyst for the oxidative coupling of hydrocarbons. In a more specific embodiment, the reactor can include a reaction zone under reaction conditions and containing a catalyst for the oxidative coupling of methane. The reactor can include a reaction zone under reaction conditions and containing catalyst for the coupling of methane with toluene. The catalyst can be an acidic, basic or neutral catalyst, and can be an acidic, basic or neutral zeolite catalyst. The reactor may employ a fluidized bed catalyst system, a fixed catalyst bed, layers of a fixed catalyst bed, or any other catalyst arrangement.

Another embodiment of the present invention is a method for the oxidative coupling of hydrocarbons that includes providing a hydrocarbon feedstream and providing an oxidative catalyst within a reactor as described herein. An additional embodiment of the present invention is a method for the oxidative coupling of methane to toluene that includes providing a hydrocarbon feedstream including methane and toluene and providing an oxidative catalyst within a reactor. The reactor in the methods of the present invention may have an inner coating or lining, which is capable of isolating the oxidative coupling reaction from contact with at least a portion of the interior walls of the reactor. In an embodiment, the coating or lining covers the majority of the parts that come into contact with the reaction mixture (also referred to as "wetted" parts) of the interior of the reactor. In an embodiment, the coating or lining may include a ceramic material, an inert sealant material, glass, quartz or combinations thereof. In alternate embodiments the reactor is treated in a manner to reduce the catalytic effects of the reactor wetted parts, such as by passivation of a portion of the reactor material of construction.

In an embodiment the hydrocarbon feedstream, containing methane, and an oxygen source are fed to the reactor wherein oxidative coupling of methane occurs over the oxidative catalyst according to a set of reaction conditions. A product stream that includes ethane and ethylene is recovered from the reactor.

In an embodiment the hydrocarbon feedstream, containing methane and toluene, and an oxygen source are fed to the reactor wherein oxidative coupling of methane to toluene occurs over the oxidative catalyst according to a set of reaction conditions. A product stream that includes styrene and ethylbenzene is recovered from the reactor.

The temperature of the methods of the present invention can range from 400° C. to 850° C., optionally from 600° C. to 750° C. In an aspect, the molar ratio of methane to oxygen can be from 1:1 to 100:1, optionally from 4:1 to 80:1. In an aspect, the molar ratio of methane to toluene can be from 1:1 to 50:1, optionally from 8:1 to 30:1. The catalyst can be pretreated in the reactor before it is used for the oxidative coupling of hydrocarbons.

The composition of the product hydrocarbons can be adjusted by adjusting the temperature of the reaction. The composition can also be adjusted by adjusting the space velocity of the reaction.

DETAILED DESCRIPTION

Figure 1:
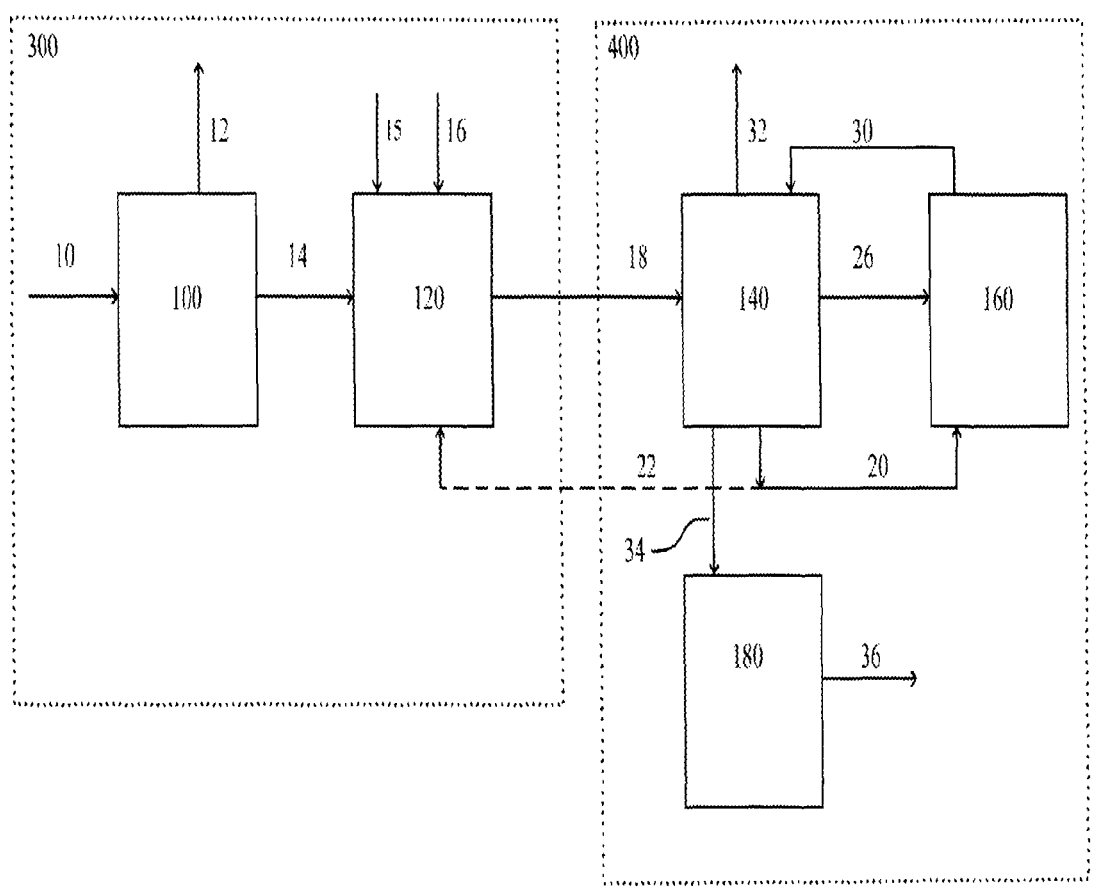
FIG. 1 is a schematic block diagram illustrating a process for making ethylbenzene and styrene.

Referring to FIG. 1, there is illustrated a schematic block diagram of one embodiment of an alkylation/transalkylation process carried out in accordance with the prior art. A feed stream of toluene is supplied via line 10 to reactive zone 100 that produces product streams of methane via line 12 and benzene via line 14. The benzene via line 14 along with ethylene via line 16 are supplied to an alkylation reactive zone 120 which produces ethylbenzene and other products which are sent via line 18 to a separation zone 140. The separation zone 140 can remove benzene via line 20 and send it to a transalkylation reaction zone 160. The benzene can also be partially recycled via line 22 to the alkylation reactive zone 120. The separation zone 140 can also remove polyethylbenzenes via line 26 which are sent to the transalkylation reaction zone 160 to produce a product with increased ethylbenzene content that can be sent via line 30 to the separation zone 140. Other byproducts can be removed from the separation zone 140 as shown by line 32, this can include methane and other hydrocarbons that can be recycled within the process, used as fuel gas, flared, or otherwise disposed of. Ethylbenzene can be removed from the separation zone 140 via line 34 and sent to a dehydrogenation zone 180 to produce styrene product that can be removed via line 36.

The front end of the process 300, designated by the dashed line, includes the initial toluene to benzene reactive zone 110 and the alkylation reactive zone 120. It can be seen that the input streams to the front end 300 can include toluene via line 10 and ethylene via line 16 and oxygen via line 15. There can also be input streams of benzene from alternate sources other than from a toluene reaction, shown as reactive zone 100, although they are not shown in this embodiment. The output streams include the methane via line 12 that is produced during the conversion of toluene to benzene in reactive zone 110 and the product stream containing ethylbenzene via line 18 that is sent to the back end of the process 400. The back end 400 includes the separation zone 140, the transalkylation reaction zone 160 and the dehydrogenation zone 180.

Figure 2:
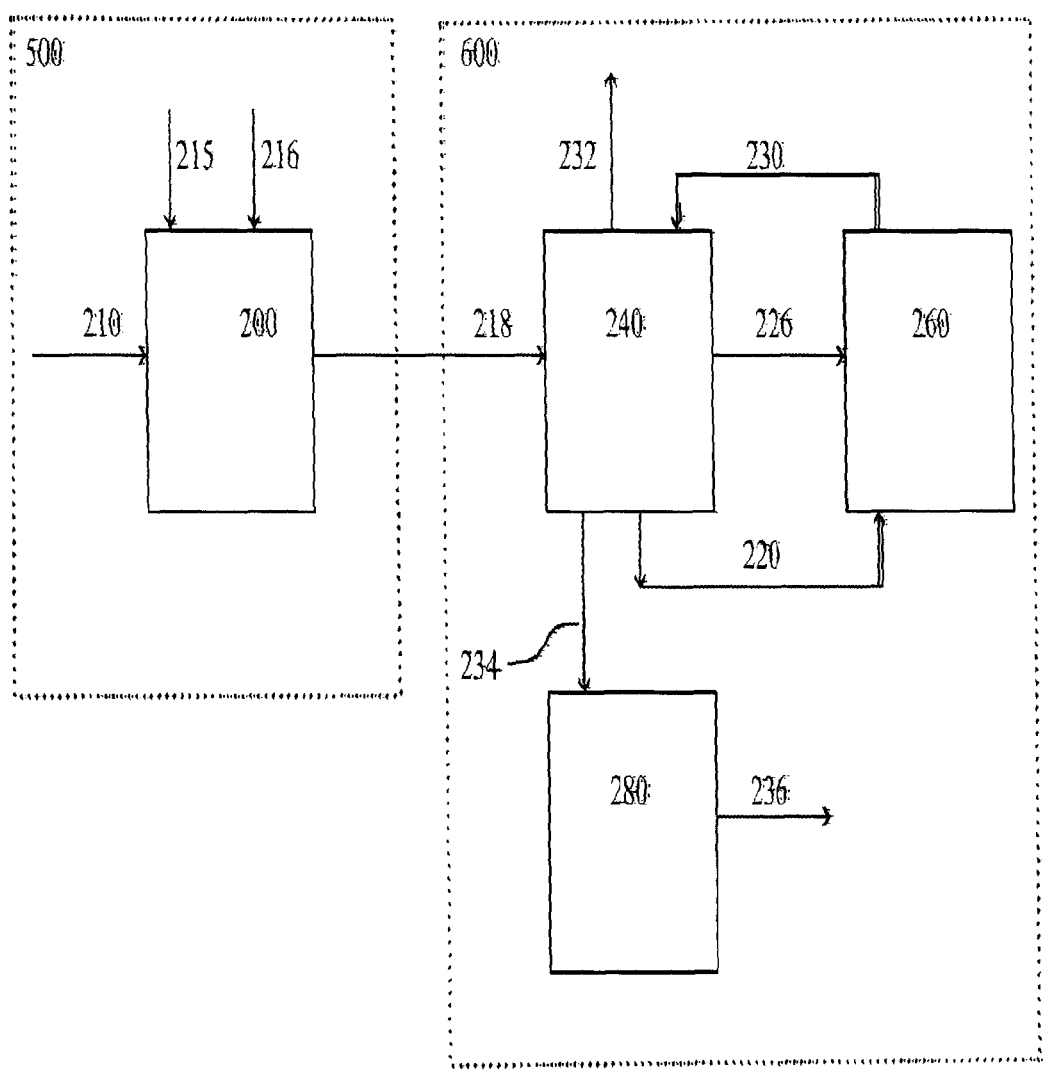
FIG. 2 is a schematic block diagram illustrating a process for making ethylbenzene and styrene according to an embodiment of the present invention.

Referring now to FIG. 2, there is illustrated a schematic block diagram of one embodiment of the present invention that involves oxidative coupling reactions of hydrocarbons. Feed streams of a hydrocarbon such as toluene supplied via line 210 and methane supplied via line 216, along with an oxygen source 215, are supplied to a reactive zone 200, which produces ethylbenzene along with other products, which can include styrene. In some embodiments an input stream of oxygen 215 may be supplied to the reactive zone 200. The output from the reactive zone 200 includes a product containing ethylbenzene, which is supplied via line 218 to a separation zone 240. The separation zone 240 can separate benzene that may be present via line 220 which can be sent to an alkylation reaction zone 260. The alkylation reaction zone 260 can include a transalkylation zone. The separation zone 240 can also remove heavy molecules that may be present via line 226. The alkylation reaction zone 260 can produce a product with increased ethylbenzene content that can be sent via line 230 to the separation zone 240. Other byproducts can be removed from the separation zone 240 as shown by line 232, this can include methane and other hydrocarbons that can be recycled within the process, used as fuel gas, flared or otherwise disposed of. Ethylbenzene can be removed from the separation zone 240 via line 234 and sent to a dehydrogenation zone 280 to produce styrene product that can be removed via line 236. Any styrene that is produced from the reactive zone 200 can be separated in the separation zone 240 and sent to the dehydrogenation zone 280 via line 234 along with the ethylbenzene product stream, or can be separated as its own product stream, (not shown), bypassing the dehydrogenation zone 280 and added to the styrene product in line 236.

The front end 500 of the embodiment of the invention shown in FIG. 2 has a single reactive zone 200 for the oxidative coupling reaction rather than the two reactive zones contained within the front end 300 shown in FIG. 1, the reactive zone 100, and the alkylation reactive zone 120. The reduction of one reactive zone can have a potential cost savings and can simplify the operational considerations of the process. The back end 600 includes the separation zone 240, the transalkylation reaction zone 260 and the dehydrogenation zone 280 that operates in the manner of the back end section as shown in FIG. 1 and described above.

The results of oxidative coupling reactions can be influenced by many factors, such as reaction conditions, source and contents of the feed, and reactor design. The catalyst used for the reaction can be one of the most important factors. The effectiveness of the reaction can be measured in terms of conversion, selectivity, and yield. Conversion refers to the percentage of reactant (e.g. methane) that undergoes a chemical reaction. Selectivity refers to the relative activity of a catalyst in reference to a particular compound in a mixture. Selectivity is quantified as the proportion of a particular product relative to all others.

The reactor vessel of the present invention may include stainless steel, carbon steel, aluminum, or any other material that may be used in the design of an oxidative reactor. It has been discovered that some materials that can be used for the interior of the reactor that come into contact with the reaction mixture (also referred to as "wetted" parts) can catalyze the transformation of hydrocarbons under oxidative reaction conditions. The catalyzing effect of the reactor interior surface in such oxidation reactors can cause the formation of undesirable oxygen containing products such as aldehydes, alcohols, ketones, carbon monoxide and carbon dioxide.

An embodiment of the present invention includes a reactor that supports the oxidative coupling of hydrocarbons by reducing the catalyzation of the hydrocarbon reactant mixture with the interior parts of the reactor under oxidative reaction conditions. The reactor of the present invention may be treated to reduce the participation of the interior parts on the reaction at reaction conditions. The reactor can be treated so the reactor itself does not substantially participate in the reaction. In an embodiment all or a portion of the interior parts are treated to passivate the parts, such as by placement of a passivation agent on a portion of the interior of the reactor. ASTM A967 provides advice for the passivation of stainless steel. In an embodiment at least a portion of the wetted parts of the interior of the reactor is treated to reduce any detrimental catalytic effects of the reactor interior.

The reactor of the present invention may have an inner coating or lining, which is capable of isolating the oxidative coupling reaction from contact with at least a portion of the interior walls of the reactor. In an aspect the inner coating or lining covers at least a portion of the parts of the interior of the reactor that come into contact with the reaction mixture (also referred to as "wetted" parts). In an embodiment, 10% to about 100% percent of the wetted parts are isolated from the reaction mixture. In another embodiment, the inner coating or lining covers the majority of the wetted parts. In a further embodiment, the inner lining or coating covers between about 75 to about 95% of the interior surface of the reactor. In a more specific embodiment, inner lining or coating covers at least 99% of the interior surface of the reactor. In an embodiment the reactor contains a coating or lining that includes an oxidative catalyst.

The coating or lining of the present invention may include a ceramic material, an inert sealant material, glass, quartz, or combinations thereof. In an embodiment, the lining or coating is capable of withstanding typical oxidation reaction conditions, including temperatures up to 1000° C. and pressures up to 500 psia. In an aspect the lining or coating is capable of withstanding temperatures ranging from about 400° C. to about 850° C. and pressures ranging from about 1 psia to about 200 psia.

In the case of a ceramic lining, the lining in the reactor can, according to the invention, suitably include an inner lining of a prefabricated ceramic material and an outer lining cast-in-situ also of ceramic material. The lining can include an inner lining of a prefabricated ceramic material and one or more outer layers of ceramic felt. In another embodiment the ceramic layer may be a pre-cast or molded refractory lining to the vessel wall by metal anchors, adhesives, or the like. A further embodiment is to apply a castable refractory lining, containing ceramic material, inside the interior of the reactor vessel.

The lining of the present invention is capable of withstanding oxidative reaction conditions. In an embodiment the reactor contains a glass lining that is capable of withstanding oxidation conditions. In further embodiment the glass lining also includes a ceramic coating. The lining of the present invention may also include quartz. The quartz may include quartz wool. The lining of the present invention may include silicic acid compound, such as that mentioned in U.S. Pat. No. 4,708,890 to Shimizu et al, which is hereby incorporated by reference in its entirety. In each case, the lining composition chosen for the reactor lining is capable of withstanding the oxidative reaction conditions.

In the case of a ceramic coating or inert sealant material, the coating can be a high temperature inert ceramic material, such as those available from Aremco Products, Inc. and sold under the Pyro-Paint trademark. In an embodiment the reactor contains a coating or lining sealant material that includes an oxidative catalyst. An oxidative catalyst can be added to an otherwise inert sealant material.

In an embodiment of the present invention the reactor contains an oxidative catalyst. The oxidative catalyst may be prepared for the oxidative coupling of hydrocarbons. In a further embodiment the oxidative catalyst is prepared to influence the conversion, selectivity, and yield of the oxidative coupling of methane and other hydrocarbons. In another aspect, the oxidative catalyst is prepared to influence the conversion, selectivity, and yield of the oxidative coupling of methane to toluene.

The reactor of the invention can include a reaction zone under reaction conditions containing a catalyst for the oxidative coupling of hydrocarbons. In a more specific embodiment, the reactor can include a reaction zone under reaction conditions and containing catalyst for the coupling of methane with toluene. The reactor can also include a reaction zone under reaction conditions containing a catalyst for reacting toluene and formaldehyde to form styrene. The catalyst can be an acidic, basic or neutral catalyst, and can be an acidic, basic or neutral zeolite catalyst. The reactor may employ a fluidized-bed catalyst system, a fixed catalyst bed, layers of a fixed catalyst bed, a catalyst containing monolith, or any other suitable catalyst arrangement.

An embodiment of the present invention is a process of oxidative coupling of methane, or OCM. The process can include steps such as preparing an oxidative catalyst, pretreating the oxidative catalyst inside a reactor, and carrying out the oxidative coupling reaction inside the reactor, according to a set of reaction conditions. Preparation and pretreatment of the catalyst and reaction conditions can influence the conversion, selectivity, and yield of OCM and other coupling reactions.

Another embodiment of the present invention is a process for the oxidative methylation of toluene (OMT), as well as the oxidative coupling of other hydrocarbons, including the steps of providing a reactor and running the reactor according to a set of reaction conditions. The process can include steps such as preparing an oxidative catalyst, pretreating the oxidative catalyst inside a reactor, and carrying out the oxidative coupling reaction inside the reactor, according to a set of reaction conditions. Preparation and pretreatment of the catalyst and reaction conditions can influence the conversion, selectivity, and yield of OMT and other coupling reactions.

One aspect of the process of the present invention involves the preparation and use of a reactor in the oxidative coupling reaction(s) of the present invention. As mentioned earlier, it has been discovered that some materials can influence the transformation of hydrocarbons under oxidative reaction conditions. The influence of the interior reactor surface in the oxidation reactors can cause the formation of undesirable oxygen containing products such as aldehydes, alcohols, ketones, carbon monoxide and carbon dioxide. Therefore, it would be desirable to reduce or eliminate the influences not attributable to the catalyst during the oxidation reaction(s). An embodiment of the present invention includes an oxidative coupling method that utilizes a reactor that supports the oxidative coupling of hydrocarbons by reducing or preventing the reactor itself from catalyzing the hydrocarbons under oxidative reaction conditions. An embodiment of the present invention includes a reactor that does not substantially participate in the reaction. The reactor of the present invention may have an inner coating or lining, which is capable of isolating the oxidative coupling reaction from contact with at least a portion of the interior walls of the reactor. In an embodiment, the coating or lining covers the majority of the parts that come into contact with the reaction mixture (also referred to as "wetted" parts) of the interior of the reactor. In a further embodiment the coating or lining covers all of the wetted parts of the interior of the reactor. The coating or lining may include a ceramic material, a pyro-paint material, glass, quartz or combinations thereof. The reactor of the present invention may be lined with the silicic acid compound of U.S. Pat. No. 4,708,890 to Shimizu et al, hereby incorporated by reference in its entirety. In an embodiment, the lining of the interior of the reactor creates an inert reactor surface with respect to the oxidative reaction.

The methods of the present invention utilizing a reactor having an inert inner lining, or coating, may be capable of achieving conversions greater than the same, or similar, reactions in a reactor, such as a stainless steel reactor, without an inert lining or coating. In an embodiment, the use of a reactor including an inert inner lining results in up to an increase in conversion percent of up to 40 wt % over the conversion percent of the same, or similar, reaction in a stainless steel reactor without an inert lining or coating. In a further embodiment, the use of a reactor including an inert inner lining results in up to an increase in conversion percent of from 2 wt % to 30 wt % over the conversion percent of the same, or similar, reaction in a stainless steel reactor without an inert lining or coating. In an aspect, the methods of the present invention include conversions of from 1 wt % to 40 wt %. In a further aspect, the methods of the present invention include conversions of from 4 wt % to 8 wt %.

The methods of the present invention utilizing a reactor having an inert inner lining, or coating, are capable of achieving a product selectivity greater than the same, or similar, reactions in a stainless steel reactor without an inert lining or coating. In an embodiment, the use of a reactor including an inert inner lining results in up to an increase in selectivity of up to 60 mol % over the percent selectivity of the same, or similar, reaction in a stainless steel reactor without an inert lining or coating. In a further embodiment, the use of a reactor including an inert inner lining results in up to an increase in selectivity of from 5% to 55% over the percent selectivity of the same, or similar, reaction in a stainless steel reactor without an inert lining or coating. In an aspect, the methods of the present invention include a product selectivity of from 20 mol % to 70 mol %. In a further aspect, the methods of the present invention include a product selectivity of from 40 mol % to 60 mol %.

In an aspect, the methods of the present invention utilizing a reactor having an inert inner lining, or coating, are capable of achieving a product having lower amounts of aldehydes, alcohols, ketones, carbon monoxide, or carbon dioxide than the same, or similar, reactions in a stainless steel reactor without an inert lining or coating. Embodiments can have a reduction of the products listed above of at least 5%, optionally at least 10%, optionally at least 25%, optionally at least 40%. In another aspect, the methods of the present invention utilizing a reactor having an inert inner lining, or coating, are capable of achieving a product having amounts of aldehydes, alcohols, ketones, carbon monoxide, and carbon dioxide of less than 50% compared with the products of the same, or similar, reactions in a stainless steel reactor without an inert lining or coating. In a further aspect, the products of the present invention do not contain aldehydes, alcohols, ketones, carbon monoxide, or carbon dioxide.

Another aspect of the process of the present invention involves the preparation of a catalyst for OCM, OMT, or other coupling reactions or combinations thereof. A catalyst of the present invention generally includes a substrate, one or more metal promoters and oxygen. The catalyst can vary in terms of its activity, useful run life, and others characteristics. This variation can be influenced by the selection of the substrate and the combination of metal promoters supported by the substrate.

The alkali or base metal compounds of the catalyst may be present in either a hydroxide or oxide form and may include lithium sodium, and other Group 1 elements; calcium, barium, and other Group 2 elements; lanthanum, cesium and other Lanthanoid group elements; as well as bismuth, lead, cadmium, titanium, and nickel which may be present either as a metal oxide, hydroxide, or in the metallic forms as a promoter. The various elements that make up the catalyst can be derived from any suitable source, such as in their elemental form, or in compounds or coordination complexes of an organic or inorganic nature, such as carbonates, oxides, hydroxides, nitrates, acetates, chlorides, phosphates, sulfides and sulfonates. The elements and/or compounds can be prepared by any suitable method, known in the art, for the preparation of such materials.

According to another embodiment, the catalyst of the present invention can include a substrate that ranges from 40 to 90 wt % of the catalyst, the substrate made of one or more of the elements of Set A consisting of: the Lanthanoid group (La, Ce, Pr, Nd, Sm, Eu, Gd, Tb, Dy, Ho, Er, Th, Yb, Lu), Mg, Ca, and the elements of Group 4 of the periodic table (Ti, Zr, and Hf). The substrate supports a first promoter that ranges from 0.01 to 40 wt % of the catalyst chosen from one or more of the elements of Set B consisting of: Li, Na, K, Rb, Cs, and the elements of Group 3 (including La and Ac) and Groups 5-15 of the periodic table. The substrate further supports a second promoter that ranges from 0.01 to 40 wt % of the catalyst chosen from one or more of the elements of Set C consisting of: Li, Na, K, Rb, Cs, Ca, Sr, and Ba. If an element from Group 1 of the periodic table (Li, Na, K, Rb, Cs) is used as a catalytic element from Set B it cannot be used as a catalytic element from Set C. The catalyst further includes Set D, which consists of oxygen, in a range of 10 to 45 wt %. All percentages are for the catalyst after calcination.

This catalyst embodiment contains at least one element from each of the Sets A, B, C, and D in the ranges given above. At least 90 wt % of the catalyst is made of the elements of Sets A, B, C and oxygen in the final catalyst composition after a calcination procedure. Optionally at least 95 wt % of the catalyst is made of the elements of Sets A, B, C and D in the final catalyst after a calcination procedure. Residual anions may be present in the final catalyst, e.g. nitrate, halide, sulfate and acetate. The catalyst can vary in terms of its activity, its basicity, its lifetime, and other characteristics. This variation can be influenced by the selection of the elements chosen from Sets A, B, C and D and their respective content in the catalyst.

The term "substrate" is not meant to indicate that this component is necessarily inactive, while the other metals and/or promoters are the active species. On the contrary, the substrate can be an active part of the catalyst. The term "substrate" would merely imply that the substrate makes up a significant quantity, generally 10% or more by weight, of the entire catalyst. The promoters individually can range from 0.01% to 60% by weight of the catalyst, optionally from 0.01% to 50%. If more than one promoters are combined, they together generally can range from 0.01% up to 70% by weight of the catalyst. The elements of the catalyst composition can be provided from any suitable source, such as in its elemental form, as a salt, as a coordination compound, etc.

The addition of a support material to improve the catalyst physical properties is possible within the present invention. Binder material, extrusion aids or other additives can be added to the catalyst composition or the final catalyst composition can be added to a structured material that provides a support structure. For example, the final catalyst composition can be supported by a structured material comprising an alumina or aluminate framework. The content of such a binder material, extrusion aids, structured material, or other additives, and their respective calcination products, will not be taken into consideration within the stated percentage ranges of Sets A-D stated herein. As an additional example a binder material, which can contain elements that are contained within Sets A-D, can be added to the catalyst composition. Upon calcination these elements can be altered, such as through oxidation which would increase the relative content of oxygen within the final catalyst structure. The binder material elements and the calcination products are not taken into consideration within the stated percentage ranges of Sets A-D stated herein. The combination of the catalyst of the present invention combined with additional elements such as a binder, extrusion aid, structured material, or other additives, and their respective calcination products, are included within the scope of the invention.

In one aspect, the invention is a method for the preparation of an oxidative catalyst for OMT, or another oxidative coupling reaction. In one embodiment, the catalyst can be prepared by combining a substrate chosen from at least one element from Set A with at least one promoter element chosen from Set B, at least one promoter element chosen from Set C, and oxygen from Set D. The present invention is not limited by the method of catalyst preparation, and all suitable methods should be considered to fall within the scope herein. Particularly effective techniques are those utilized for the preparation of solid catalysts. Conventional methods include coprecipitation from an aqueous, an organic or a combination solution-dispersion, impregnation, dry mixing, wet mixing or the like, alone or in various combinations. In general, any method can be used which provides compositions of matter containing the prescribed components in effective amounts. According to an embodiment the substrate is charged with promoter via an incipient wetness impregnation. Other impregnation techniques such as by soaking, pore volume impregnation, or percolation can optionally be used. Alternate methods such as ion exchange, wash coat, precipitation, and gel formation can also be used. Various methods and procedures for catalyst preparation are listed in the technical report Manual of Methods and Procedures for Catalyst Characterization by J. Haber, J. H. Block and B. Dolmon, published in the International Union of Pure and Applied Chemistry, Volume 67, Nos 8/9, pp. 1257-1306, 1995, incorporated herein in its entirety.

In an embodiment, the substrate can be a metal oxide of one or more elements of Set A. One example of an oxide substrate useful for the present invention is magnesium oxide, MgO. The oxide substrate can be either obtained commercially or produced in the lab. For instance, a metal oxide can be made by thermal decomposition of its corresponding salt at elevated temperatures up to 750° C. The choice of precursor from which the oxide substrate is produced can have some effect on the performance of the eventual catalyst.

When slurries, precipitates or the like are prepared, they will generally be dried, usually at a temperature sufficient to volatilize the water or other carrier, such as about 100° C. to about 250° C. Irrespective of how the components are combined and irrespective of the source of the components, the dried composition is generally calcined in the presence of a oxygen-containing gas, usually at temperatures between about 300° C. and about 900° C. for from 1 to about 24 hours. The calcination can be in a reducing or inert atmosphere or an oxygen-containing atmosphere.

The prepared catalyst can be ground, pressed, sieved, shaped and/or otherwise processed into a form suitable for loading into a reactor. The reactor can be any type known in the art to make catalyst particles, such as a fixed bed, fluidized bed, or swing bed reactor. The reactor set-up can optionally include a recycle stream. Optionally an inert material, such as quartz chips, can be used to support the catalyst bed and to place the catalyst within the bed.

Depending on the catalyst, a pretreatment of the catalyst may, or may not, be necessary. In one embodiment the invention involves the pretreatment of an oxidative catalyst for OCM, OMT, or another oxidative coupling reaction. For the pretreatment, the reactor can be heated elevated temperatures, such as 800° C. to 900° C. with an air flow, such as 100 mL/min, and held at these conditions for a length of time, such as 1 to 3 hours. Then, the reactor can be cooled down to a temperature of around the operating temperature of the reactor, for example 500° C. to 650° C., or optionally down to atmospheric or other desired temperature. The reactor can be kept under an inert purge, such as under helium.

In another aspect, the invention involves reaction conditions for OCM, OMT, or another oxidative coupling reaction. Several parameters including feed composition, molar ratio of hydrocarbon reactant to oxygen, temperature, pressure, time on stream, preparation method, particle size, porosity, surface area, contact time and others can influence the outcome of the reaction. For almost every reaction condition, there can be a range of values best suited to oxidative coupling. Measures are generally taken to increase conversion and selectivity.

Although contaminants that might significantly interfere with the oxidative coupling reaction should be avoided, the addition of trace quantities of a reaction modulator may be useful. Reaction modulators can be used for the control or alteration of conversion, selectivity, or activity of a particular catalyst or in response to certain reaction conditions. Non-limiting examples of possible reaction modulators include chlorine, ethylene and carbon monoxide.

Inert diluents such as helium and nitrogen may be included in the feed to adjust the gas partial pressures. Optionally, $CO_2$ or water (steam) can be included in the feed stream as these components may have beneficial properties, such as in the prevention of coke deposits. The pressure for oxidative coupling reactions can generally range from 1 psia to 200 psia or more. The reaction pressure is not a limiting factor regarding the present invention and any suitable condition is considered to be within the scope of the invention.

The temperature for oxidative coupling reactions can generally range from 400° C. to 850° C., optionally from 600° C. to 750° C., optionally from 550° C. to 700° C. The reaction temperature is not a limiting factor regarding the present invention and any suitable condition is considered to be within the scope of the invention.

Any suitable space velocity can be considered to be within the scope of the invention. As used herein the space velocity shall be defined as: space velocity=[feed flow as vapor ($cm^3$/h)]/[catalyst weight (g)]. A standard reference temperature and pressure (72° F. and 14.7 psia) is used to convert a liquid under these conditions, such as toluene, to a feed vapor flow. For example: 0.076 $cm^3$/min of liquid toluene is converted into moles and then using 22.4 L/mol (as if it were an ideal gas) it is converted into a vapor flow of 16 $cm^3$/min. The space velocity can generally range from 15,000 $cm^3g^{-1}h^{-1}$ to 100,000 $cm^3g^{-1}h^{-1}$, optionally from 20,000 $cm^3g^{-1}h^{-1}$ to 85,000 $cm^3g^{-1}h^{-1}$. This range is an indication of possible space velocities, such as for a fixed bed reactor. Of course altering the catalyst composition, the amount of inert material, etc can alter the space velocity outside of this range. Also a change in the reactor from a fixed bed to an alternate design, such as a fluidized bed can also dramatically change the relative space velocity and can be outside of the stated range above. The space velocity ranges given are not limiting on the present invention and any suitable condition is considered to be within the scope of the invention.

In the case of OCM, the reaction temperatures generally range from 400° C. to 850° C., optionally from 600° C. to 750° C., optionally from 550° C. to 700° C. The reaction temperature is not a limiting factor regarding the present invention and any suitable condition is considered to be within the scope of the invention. The contents of the feed can include methane and an oxygen source. The methane to oxygen molar ratio can range from 1:1 to 100:1, optionally from 4:1 to 80:1.

In the case of OMT, the feed will include toluene along with methane and oxygen. The toluene can be vaporized and introduced to the reactor either by passing the oxygen and methane gas mixture through a toluene vapor saturator right before the inlet of the reactor tube, or by syringe-pumping the liquid toluene into the gas flow and vaporizing it in a pre-heated zone (250~300° C.) before entering the reactor. The methane to oxygen molar ratio can range from 1:1 to 100:1, optionally from 4:1 to 80:1. The molar ratio of methane to toluene can be from 1:1 to 50:1, optionally from 8:1 to 30:1. Temperature can be from 300° C. to 900° C., optionally from 300° C. to 800° C., optionally from 350° C. to 750° C.

In an OMT oxidative coupling reaction, methane and toluene are considered the main reactants of OMT and oxygen can be another important component of the feed. Oxygen is a required component of the feed for oxidative coupling. Methane can be obtained from natural gas, or from organic sources, such as the decomposition of waste through fermentation. Whatever the source, methane used in OCM and OMT should not contain contaminants that might significantly interfere or give a detrimental effect on the oxidative coupling reaction. The oxygen source can be any source suitable for providing oxygen to the reaction zone such as pure oxygen, oxygen-enriched air, or air. Alternate sources of oxygen may also be used, such as nitrobenzene, nitrous oxide or other oxygen containing compounds. The gas containing oxygen should not contain any contaminants that might significantly interfere with the oxidative coupling reaction.

For the OMT reaction of the present invention, the methane to oxygen molar ratio can be from 1:1 to 30:1, optionally from 4:1 to 10:1. Oxygen can be fed intermittently, alternating with the hydrocarbon stream or optionally can be fed simultaneously into the reactor with the hydrocarbon reactants.

Products leaving the reactor can be monitored with gas chromatography, or by some other method. Products can be separated using distillation or some other method.

EXAMPLES

The following examples are intended to give a better understanding of the present invention in its many embodiments, but are not intended to limit the scope of the invention in any way.

Experimentations shows the utility of a ceramic lining by comparing the products of oxidative coupling reactions in stainless steel, quartz, and ceramic-lined stainless steel reactors. Each case utilized the same catalyst and same reaction conditions. The feedstocks used were methane, toluene, and oxygen. These feedstocks were used to produce styrene and/or ethylbenzene as a result of carbon-carbon bond formation.

The details for the stainless steel reactor in carrying out the OMT reaction of the example is as follows. A stainless steel reactor with 0.5 inch outer diameter and 0.465 inch internal diameter was filled with silicon carbide (to a height of about 12.5 inches), then a bed of alumina (to a height of 2.125 inches; 2 mL) then followed by the catalyst (to a height of 2.0 inches; 1.5 mL) of size ranging from 250-425 μm, then a bed of alumina (to a height of 1.625 inches; 3 mL) and then more silicon carbide (of a height of about 7.75 inches) such that a 0.125 inch stainless steel thermowell was positioned in the middle of the bed.

The details for the quartz reactor in carrying out OMT reaction of the example is as follows. A quartz reactor (0.75 inch outer diameter and 30.0 inch long) was fitted with a thermowell (0.25 inch outer diameter and 13.5 inch long) in the middle of the catalyst bed. The reactor was loaded according to the following sequence. First quart wool was placed in the bottom, then quartz chips (0.5 inches and 2 mL) and then catalyst (0.57 g; 1 mL), which was about 0.25 inches in height.

The details for the stainless steel with ceramic liner insert reactor in carrying out OMT reaction of the example is as follows. A 0.75 inch outer diameter, 0.71 inch internal diameter and 33.0 inch long stainless steel reactor and a 0.125 inch wide and 17.0 inch long stainless steel thermowell were heated to 850° C. for 13 h. The walls were then sand blasted and rinsed with n-hexane. The cleaned reactor and thermowell were dried at room temperature and then were coated with pyropaint. A 0.68 inch outer diameter, 0.5 inch internal diameter and 33.0 inch long ceramic liner was inserted into the cleaned and coated reactor. The ceramic insert reactor was cured at room temperature for 2h and then was gradually heated to 800° C. at 2° C./min and was held at 800° C. for 2h and then was cooled to room temperature before it was used. The thermowell was coated with pyropaint and was cured as described above.

The catalyst syntheses for carrying out OMT reactions is given below. The Ba/MgO catalyst was used in the oxidative coupling of methane and the oxidative methylation of toluene. The catalyst included 5% Ba by weight and was prepared from barium nitrate (6.53 g) (Sigma Aldrich, 98.0%) and MgO (23.46 g) (Fisher, 99%) by incipient wetness impregnation methodology in aqueous solution. The mixture was dried at 120° C. for 3 h and then calcined at 850° C. in air for 1 h.

The Mn, $NaWO_4$/MgO catalyst was prepared by sol gel method from $Mg(OH)_2$ (Aldrich 99.8%), Mn(II) nitrate (Mn (II) nitrate 50.48% solution), and sodium meta tungstate solution $(Na_2WO_4)_9WO_3.H_2O)$. A solution of magnesium hydroxide (15.2 g) in water (14.725 mL) was heated on a hot plate and then 2.0 g of Mn(II) nitrate (Mn(II) nitrate 50.48% solution) was added slowly (~5 minutes) and constantly stirring. To this hot mixture a solution of sodium meta tungstate solution $(Na_2WO_4)_9WO_3 \cdot H_2O)$ 0.87 g in 8 mL of water was prepared and added slowly. The mixture was now stirred constantly to boil off water until precipitation was formed. The precipitate was then transferred into a dish and dried at 110° C. for 12 h. The mixture is then ground with 2% methyl cellulose and water (10 mL) to form a wet paste and binding agent (cement. ~0.5 g) was added to form a fine paste. The paste was dried at 110° C. and calcined at 775° C. for 4h.

The results in Table 1 indicate that selectivity to the formation of carbon-carbon bonds is improved by using a more inert reactor surface such as quartz or ceramic lining.

TABLE 1

| Reactor type | Catalyst | Temperature (° C.) | Toluene Conversion (wt %) | Selectivity (mol %) | | | |
|---|---|---|---|---|---|---|---|
| | | | | Benzene | EB | Styrene | EB + Styrene |
| Stainless steel | Mn, NaWO$_4$/ MgO | 760 | 2.2 | 48.0 | 0.0 | 48.0 | 48.0 |
| Quartz | BaO/MgO | 650 | 9.8 | 49.3 | 6.9 | 41.3 | 48.2 |
| Ceramic lined | BaO/MgO | 650 | 6.3 | 23.6 | 27.6 | 33.6 | 57.2 |

Styrene is most commonly the desired product of OMT. However, depending on demand and process needs, other products can also be desired. Ethylbenzene, for instance, can be a desired product as the technology is well established for its conversion to styrene via dehydrogenation. It is thus a useful feature of this process that product distribution can be affected by modulation of reaction conditions such as temperature.

The term "conversion" refers to the percentage of reactant (e.g. toluene) that undergoes a chemical reaction.

The term "$C_2$ selectivity" as used herein is the cumulative selectivity of acetylene, ethane, and ethylene.

The term "selectivity" refers to the relative activity of a catalyst in reference to a particular compound in a mixture. Selectivity is quantified as the proportion of a particular product relative to all other products.

The abbreviation of "OCM" as used herein refers to oxidative coupling of methane. For instance, methane can couple with methane to form higher hydrocarbons such as ethane or ethylene.

The abbreviation of "OMT" as used herein refers to the oxidative methylation of toluene to form new compounds. For instance, toluene can couple with methane to form ethylbenzene and/or styrene.

Use of the term "optionally" with respect to any element of a claim is intended to mean that the subject element is required, or alternatively, is not required. Both alternatives are intended to be within the scope of the claim. Use of broader terms such as includes, includes, having, etc. should be understood to provide support for narrower terms such as consisting of, consisting essentially of, included substantially of, etc.

As used herein the space velocity shall be defined as: space velocity=[feed flow as vapor (cm$^3$/h)]/[catalyst weight (g)].

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A method for the oxidative coupling of hydrocarbons comprising:
   providing a hydrocarbon feedstream and a reactor;
   providing an oxidative catalyst within the reactor;
   feeding the hydrocarbon feedstream and an oxygen source to the reactor;
   carrying out oxidative coupling of hydrocarbons over the oxidative catalyst according to a set of reaction conditions; and
   recovering product hydrocarbons from the reactor;
   wherein the reactor does not provide a significant detrimental catalyzing effect;
   supplying the product hydrocarbons to a separation zone in fluid communication with the reactor;
   in the separation zone, separating benzene from the product hydrocarbons and sending the benzene to an alkylation zone in fluid communication with the separation zone;
   in the alkylation zone, producing a product with increased ethylbenzene;
   in the separation zone, separating ethylbenzene from the product hydrocarbons and sending the ethylbenzene to a dehydrogenation zone in fluid communication with the separation zone; and
   in the dehydrogenation zone, producing a styrene product.

2. The method of claim 1, wherein the reactor comprises an inner lining that covers a majority of wetted parts of the reactor.

3. The method of claim 2, wherein the inner lining is selected from the group consisting of an inert sealant material, glass, quartz, a ceramic material, and combinations thereof.

4. The method of claim 2, wherein the inner lining comprises an oxidative catalyst.

5. The method of claim 2, wherein the inner lining results in an increase in conversion percent of from 2 wt% to 30 wt% over the conversion percent of the same, or similar, reaction in a reactor without an inert lining or coating.

6. The method of claim 2, wherein the inner lining results in an increase in selectivity to the combination of styrene and ethylbenzene over the selectivity to the combination of styrene and ethylbenzene of the same, or similar, reaction in a reactor without an inert lining or coating.

7. The method of claim 1, having selectivity to the combination of styrene and ethylbenzene from 20 mol% to 99 mol%.

8. The method of claim 1, wherein the feedstream includes methane and the product hydrocarbons include $C_2$ hydrocarbons.

9. The method of claim 1, wherein the oxidative coupling includes oxidative coupling of methane and occurs in the reactor at a temperature of from 400° C. to 850° C.

10. The method of claim 1, wherein the feedstream includes toluene and the product hydrocarbons include ethylbenzene and styrene.

11. The method of claim 10, wherein the molar ratio of methane to toluene can be from 1:1 to 50:1.

12. The method of claim 1, wherein the oxidative coupling includes oxidative coupling of methane and a hydrocarbon other than methane and occurs in the reactor at a temperature of from 400° C. to 850° C.

13. The method of claim 1, wherein the molar ratio of hydrocarbons to oxygen ranges from 1:1 to 100:1.

14. The method of claim 1, wherein the reactor is treated to passivate portions of the reactor that contact the hydrocarbon feedstock or product hydrocarbons.

15. The method of claim 14, wherein the passivation of portions of the reactor results in an increase in selectivity to the combination of styrene and ethylbenzene over the selectivity to the combination of styrene and ethylbenzene of the same, or similar, reaction in a reactor without passivation.

16. The method of claim 1, wherein the reactor has a single reactive zone.

17. The method of claim 1, wherein the alkylation zone includes a transalkylation zone.

18. The method of claim 1, further comprising sending the product with increased ethylbenzene from the alkylation zone to the separation zone.

19. A reactor for the oxidative coupling of hydrocarbons comprising:
   a reactor vessel having a reaction contact surface;
   an inlet for feeding at least one hydrocarbon feedstream;
   an inlet for providing an oxygen source; and
   an outlet for recovering a product from the reactor; and
   wherein the reaction contact surface of the reactor vessel does not provide a significant detrimental catalyzing effect under conditions for the oxidative coupling of hydrocarbons;
   wherein the reactor is in fluid communication with a separation zone, wherein the product flows from the reactor into the separation zone, wherein the separation zone is in fluid communication with an alkylation reaction zone and a dehydrogenation zone.

20. The reactor of claim 19, wherein the reactor has a single reactive zone.

* * * * *